(12) United States Patent
Schuchman et al.

(10) Patent No.: US 7,750,050 B2
(45) Date of Patent: Jul. 6, 2010

(54) CHAPERONE-BASED THERAPY FOR NIEMANN-PICK DISEASE

(75) Inventors: Edward H. Schuchman, Haworth, NJ (US); Robert J. Desnick, New York, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 1543 days.

(21) Appl. No.: 10/998,270

(22) Filed: Nov. 24, 2004

(65) Prior Publication Data
US 2005/0153934 A1 Jul. 14, 2005

Related U.S. Application Data

(60) Provisional application No. 60/525,497, filed on Nov. 25, 2003.

(51) Int. Cl.
*A61K 31/16* (2006.01)
*C12N 9/99* (2006.01)
(52) U.S. Cl. ...................................... 514/625; 435/184
(58) Field of Classification Search ................. 514/625; 435/184
See application file for complete search history.

(56) References Cited

U.S. PATENT DOCUMENTS

| | | | |
|---|---|---|---|
| 4,816,450 A | 3/1989 | Bell et al. | |
| 4,937,232 A | 6/1990 | Bell et al. | |
| 5,220,043 A | 6/1993 | Dong et al. | |
| 5,227,508 A | 7/1993 | Kozikowski et al. | |
| 5,369,030 A | 11/1994 | Hannun et al. | |
| 5,397,788 A | 3/1995 | Horwell et al. | |
| 5,686,240 A | 11/1997 | Schuchman et al. | |
| 5,773,278 A | 6/1998 | Schuchman et al. | |
| 5,830,916 A | 11/1998 | Hannun et al. | |
| 5,851,782 A | 12/1998 | Hannun et al. | |
| 6,218,390 B1 | 4/2001 | Lagu et al. | |
| 6,255,336 B1 | 7/2001 | Shatman et al. | |
| 6,541,218 B1 | 4/2003 | Schuchman et al. | |
| 6,610,835 B1 | 8/2003 | Liotta et al. | |
| 2003/0133904 A1 | 7/2003 | Dagan et al. | |

FOREIGN PATENT DOCUMENTS

WO  WO-03/027058  4/2003

OTHER PUBLICATIONS

Tamura et al. "Mutation in aspartic acid residues modifies catalytic and hemolytic activities of *Bacillus cereus* sphingomyelinase" Biochemical Journal, 1995, vol. 309, No. 3, p. 757-764.
International Search Report for PCT/US04/41345, dated Nov. 18, 2005.
"Structural and Stereochemical Studies of Potent Inhibitors of Glucosylceramide Synthase and Tumor Cell Growth", Akira Abe et al., Journal of Lipid Research, vol. 36, 1995, pp. 611-621.
"Analysis of the Lung Pathology and Alveolar Macrophage Function in the Acid Sphingomyelinase-Deficient Mouse Model of Niemann-Pick Disease", Rajwinder Dhami, et al., Laboratory Investigation, Jul. 2001, vol. 81, No. 7, pp. 987-999.
Suchi, et al, 1992. "Retroviral-Mediated Transfer of the Human Acid Sphingomyelinase cDNA Correction of the Metabolic Defect in Cultured Niemann-Pick Disease Cells" Proc Natl Acad Sci USA 89(8): 3227-3231.
Fan et al., "Accelerated transport and maturation of lysosomal α-galactosidase A in Fabry lymphoblasts by an enzyme inhibitor," *Nature Medicine* 1999, 5:112-115.
Fan et al., "Cell-Based Screening of Active-Site Specific Chaperone for the Treatment of Fabry Disease," *Methods in Enzymology* 2003, 363:412-420.
Shin et al., "Screening for pharmacological chaperones in Fabry disease," *Biochemical and Biophysical Research Communications* 2007, 359:167-173.
Jones et al., "Characterization of common *SMPD1* mutations causing types A and B Niemann-Pick disease and generation of mutation-specific mouse models," *Molecular Genetics and Metabolism* 2008, 95:152-162.

*Primary Examiner*—Sreeni Padmanabhan
*Assistant Examiner*—Samira Jean-Louis
(74) *Attorney, Agent, or Firm*—Fish & RIchardson P.C.

(57) ABSTRACT

The present invention provides a method for treating individuals affected with the acid sphingomyelinase-deficient forms of Niemann-Pick disease (i.e., Type A or Type B Niemann-Pick) by administering small molecules as specific molecular "chaperones" for the deficient acid sphingomyelinase (ASM) enzyme associated with the disease. The molecules are ceramide, sphingomyelin, or phosphonucleotide analogues.

10 Claims, 5 Drawing Sheets

Figure 2A-D
A.
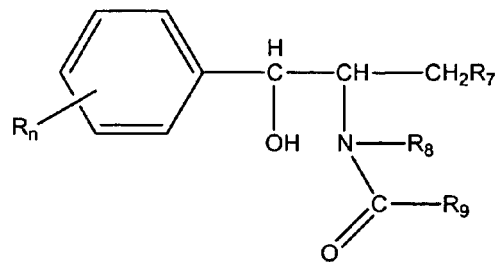
B.
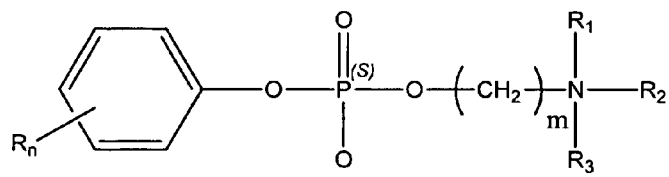
C.
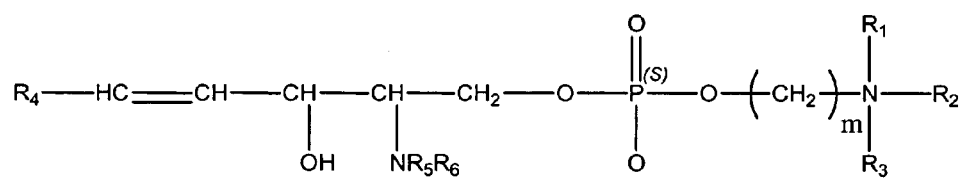
D.
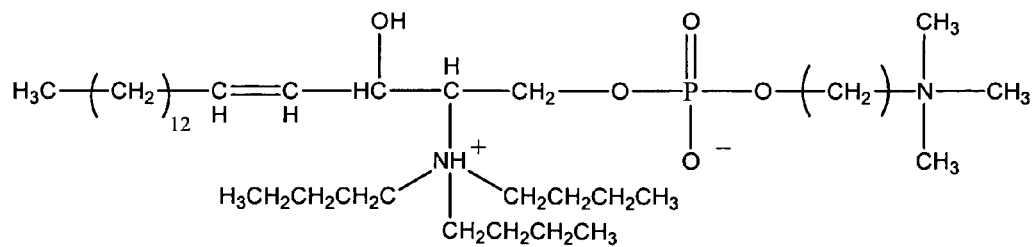

EFFECT OF D-MAPP ON ACTIVITY OF PURE ASM

EFFECT OF D-MAPP ON RESIDUAL ASM ACTIVITY IN
SKIN FIBROBLASTS FROM A TYPE A NPD PATIENT
HOMOZYGOUS FOR THE R496L MUTATION

SEQUENCE LISTING

```
<160> NUMBER OF SEQ ID NOS: 4

<210> SEQ ID NO 1
<211> LENGTH: 629
<212> TYPE: PRT
<213> ORGANISM: Homo sapiens

<400> SEQUENCE: 1

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ala Leu Ser
            35                  40                  45

Asp Ser Arg Val Leu Trp Ala Pro Ala Glu Ala His Pro Leu Ser Pro
        50                  55                  60

Gln Gly His Pro Ala Arg Leu His Arg Ile Val Pro Arg Leu Arg Asp
65                  70                  75                  80

Val Phe Gly Trp Gly Asn Leu Thr Cys Pro Ile Cys Lys Gly Leu Phe
                85                  90                  95

Thr Ala Ile Asn Leu Gly Leu Lys Lys Glu Pro Asn Val Ala Arg Val
                100                 105                 110

Gly Ser Val Ala Ile Lys Leu Cys Asn Leu Leu Lys Ile Ala Pro Pro
            115                 120                 125

Ala Val Cys Gln Ser Ile Val His Leu Phe Glu Asp Asp Met Val Glu
        130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Ser Pro Pro
            180                 185                 190

Ala Pro Gly Ala Pro Val Ser Arg Ile Leu Phe Leu Thr Asp Leu His
            195                 200                 205

Trp Asp His Asp Tyr Leu Glu Gly Thr Asp Pro Asp Cys Ala Asp Pro
        210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                245                 250                 255

Leu Glu Ser Leu Leu Ser Gly Leu Gly Pro Ala Gly Pro Phe Asp Met
            260                 265                 270

Val Tyr Trp Thr Gly Asp Ile Pro Ala His Asp Val Trp His Gln Thr
        275                 280                 285

Arg Gln Asp Gln Leu Arg Ala Leu Thr Thr Val Thr Ala Leu Val Arg
    290                 295                 300
```

```
Lys Phe Leu Gly Pro Val Pro Val Tyr Pro Ala Val Gly Asn His Glu
305                 310                 315                 320

Ser Ile Pro Val Asn Ser Phe Pro Pro Phe Ile Glu Gly Asn His
            325                 330                 335

Ser Ser Arg Trp Leu Tyr Glu Ala Met Ala Lys Ala Trp Glu Pro Trp
                340                 345                 350

Leu Pro Ala Glu Ala Leu Arg Thr Leu Arg Ile Gly Gly Phe Tyr Ala
            355                 360                 365

Leu Ser Pro Tyr Pro Gly Leu Arg Leu Ile Ser Leu Asn Met Asn Phe
        370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
                405                 410                 415

Gly Asp Lys Val His Ile Ile Gly His Ile Pro Pro Gly His Cys Leu
            420                 425                 430

Lys Ser Trp Ser Trp Asn Tyr Tyr Arg Ile Val Ala Arg Tyr Glu Asn
        435                 440                 445

Thr Leu Ala Ala Gln Phe Phe Gly His Thr His Val Asp Glu Phe Glu
    450                 455                 460

Val Phe Tyr Asp Glu Glu Thr Leu Ser Arg Pro Leu Ala Val Ala Phe
465                 470                 475                 480

Leu Ala Pro Ser Ala Thr Thr Tyr Ile Gly Leu Asn Pro Gly Tyr Arg
                485                 490                 495

Val Tyr Gln Ile Asp Gly Asn Tyr Ser Arg Ser Ser His Val Val Leu
            500                 505                 510

Asp His Glu Thr Tyr Ile Leu Asn Leu Thr Gln Ala Asn Ile Pro Gly
        515                 520                 525

Ala Ile Pro His Trp Gln Leu Leu Tyr Arg Ala Arg Glu Thr Tyr Gly
    530                 535                 540

Leu Pro Asn Thr Leu Pro Thr Ala Trp His Asn Leu Val Tyr Arg Met
545                 550                 555                 560

Arg Gly Asp Met Gln Leu Phe Gln Thr Phe Trp Phe Leu Tyr His Lys
                565                 570                 575

Gly His Pro Pro Ser Glu Pro Cys Gly Thr Pro Cys Arg Leu Ala Thr
            580                 585                 590

Leu Cys Ala Gln Leu Ser Ala Arg Ala Asp Ser Pro Ala Leu Cys Arg
        595                 600                 605

His Leu Met Pro Asp Gly Ser Leu Pro Glu Ala Gln Ser Leu Trp Pro
    610                 615                 620

Arg Pro Leu Phe Cys
625

<210> SEQ ID NO 2
<211> LENGTH: 629
<212> TYPE: PRT
<213> ORGANISM: Homo sapiens

<400> SEQUENCE: 2

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ala Leu Ser
        35                  40                  45
```

```
Asp Ser Arg Val Leu Trp Ala Pro Ala Glu Ala His Pro Leu Ser Pro
    50                  55                  60

Gln Gly His Pro Ala Arg Leu His Arg Ile Val Pro Arg Leu Arg Asp
65                  70                  75                  80

Val Phe Gly Trp Gly Asn Leu Thr Cys Pro Ile Cys Lys Gly Leu Phe
                85                  90                  95

Thr Ala Ile Asn Leu Gly Leu Lys Lys Glu Pro Asn Val Ala Arg Val
            100                 105                 110

Gly Ser Val Ala Ile Lys Leu Cys Asn Leu Leu Lys Ile Ala Pro Pro
        115                 120                 125

Ala Val Cys Gln Ser Ile Val His Leu Phe Glu Asp Met Val Glu
    130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Ser Pro Pro
            180                 185                 190

Ala Pro Gly Ala Pro Val Ser Arg Ile Leu Phe Leu Thr Asp Leu His
        195                 200                 205

Trp Asp His Asp Tyr Leu Glu Gly Thr Asp Pro Asp Cys Ala Asp Pro
    210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                245                 250                 255

Leu Glu Ser Leu Leu Ser Gly Leu Gly Pro Ala Gly Pro Phe Asp Met
            260                 265                 270

Val Tyr Trp Thr Gly Asp Ile Pro Ala His Asp Val Trp His Gln Thr
        275                 280                 285

Arg Gln Asp Gln Leu Arg Ala Leu Thr Thr Val Thr Ala Leu Val Arg
    290                 295                 300

Lys Phe Leu Gly Pro Val Pro Val Tyr Pro Ala Val Gly Asn His Glu
305                 310                 315                 320

Ser Ile Pro Val Asn Ser Phe Pro Pro Phe Ile Glu Gly Asn His
                325                 330                 335

Ser Ser Arg Trp Leu Tyr Glu Ala Met Ala Lys Ala Trp Glu Pro Trp
            340                 345                 350

Leu Pro Ala Glu Ala Leu Arg Thr Leu Arg Ile Gly Gly Phe Tyr Ala
        355                 360                 365

Leu Ser Pro Tyr Pro Gly Leu Arg Leu Ile Ser Leu Asn Met Asn Phe
    370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
                405                 410                 415

Gly Asp Lys Val His Ile Ile Gly His Ile Pro Pro Gly His Cys Leu
            420                 425                 430

Lys Ser Trp Ser Trp Asn Tyr Tyr Arg Ile Val Ala Arg Tyr Glu Asn
        435                 440                 445

Thr Leu Ala Ala Gln Phe Phe Gly His Thr His Val Asp Glu Phe Glu
    450                 455                 460
```

```
Val Phe Tyr Asp Glu Glu Thr Leu Ser Arg Pro Leu Ala Val Ala Phe
465                 470                 475                 480

Leu Ala Pro Ser Ala Thr Thr Tyr Ile Gly Leu Asn Pro Gly Tyr Leu
            485                 490                 495

Val Tyr Gln Ile Asp Gly Asn Tyr Ser Arg Ser Ser His Val Val Leu
        500                 505                 510

Asp His Glu Thr Tyr Ile Leu Asn Leu Thr Gln Ala Asn Ile Pro Gly
    515                 520                 525

Ala Ile Pro His Trp Gln Leu Leu Tyr Arg Ala Arg Glu Thr Tyr Gly
530                 535                 540

Leu Pro Asn Thr Leu Pro Thr Ala Trp His Asn Leu Val Tyr Arg Met
545                 550                 555                 560

Arg Gly Asp Met Gln Leu Phe Gln Thr Phe Trp Phe Leu Tyr His Lys
                565                 570                 575

Gly His Pro Pro Ser Glu Pro Cys Gly Thr Pro Cys Arg Leu Ala Thr
            580                 585                 590

Leu Cys Ala Gln Leu Ser Ala Arg Ala Asp Ser Pro Ala Leu Cys Arg
        595                 600                 605

His Leu Met Pro Asp Gly Ser Leu Pro Glu Ala Gln Ser Leu Trp Pro
    610                 615                 620

Arg Pro Leu Phe Cys
625

<210> SEQ ID NO 3
<211> LENGTH: 629
<212> TYPE: PRT
<213> ORGANISM: Homo sapiens

<400> SEQUENCE: 3

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ala Leu Ser
        35                  40                  45

Asp Ser Arg Val Leu Trp Ala Pro Ala Glu Ala His Pro Leu Ser Pro
50                  55                  60

Gln Gly His Pro Ala Arg Leu His Arg Ile Val Pro Arg Leu Arg Asp
65                  70                  75                  80

Val Phe Gly Trp Gly Asn Leu Thr Cys Pro Ile Cys Lys Gly Leu Phe
                85                  90                  95

Thr Ala Ile Asn Leu Gly Leu Lys Lys Glu Pro Asn Val Ala Arg Val
            100                 105                 110

Gly Ser Val Ala Ile Lys Leu Cys Asn Leu Leu Lys Ile Ala Pro Pro
        115                 120                 125

Ala Val Cys Gln Ser Ile Val His Leu Phe Glu Asp Asp Met Val Glu
    130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Ser Pro Pro
            180                 185                 190

Ala Pro Gly Ala Pro Val Ser Arg Ile Leu Phe Leu Thr Asp Leu His
        195                 200                 205
```

-continued

```
Trp Asp His Asp Tyr Leu Glu Gly Thr Asp Pro Asp Cys Ala Asp Pro
210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                245                 250                 255

Leu Glu Ser Leu Leu Ser Gly Leu Gly Pro Ala Gly Pro Phe Asp Met
            260                 265                 270

Val Tyr Trp Thr Gly Asp Ile Pro Ala His Asp Val Trp His Gln Thr
        275                 280                 285

Arg Gln Asp Gln Leu Arg Ala Leu Thr Thr Val Thr Ala Pro Val Arg
    290                 295                 300

Lys Phe Leu Gly Pro Val Pro Val Tyr Pro Ala Val Gly Asn His Glu
305                 310                 315                 320

Ser Ile Pro Val Asn Ser Phe Pro Pro Phe Ile Glu Gly Asn His
                325                 330                 335

Ser Ser Arg Trp Leu Tyr Glu Ala Met Ala Lys Ala Trp Glu Pro Trp
                340                 345                 350

Leu Pro Ala Glu Ala Leu Arg Thr Leu Arg Ile Gly Gly Phe Tyr Ala
            355                 360                 365

Leu Ser Pro Tyr Pro Gly Leu Arg Leu Ile Ser Leu Asn Met Asn Phe
        370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
                405                 410                 415

Gly Asp Lys Val His Ile Ile Gly His Ile Pro Pro Gly His Cys Leu
                420                 425                 430

Lys Ser Trp Ser Trp Asn Tyr Tyr Arg Ile Val Ala Arg Tyr Glu Asn
            435                 440                 445

Thr Leu Ala Ala Gln Phe Phe Gly His Thr His Val Asp Glu Phe Glu
        450                 455                 460

Val Phe Tyr Asp Glu Glu Thr Leu Ser Arg Pro Leu Ala Val Ala Phe
465                 470                 475                 480

Leu Ala Pro Ser Ala Thr Thr Tyr Ile Gly Leu Asn Pro Gly Tyr Arg
                485                 490                 495

Val Tyr Gln Ile Asp Gly Asn Tyr Ser Arg Ser Ser His Val Val Leu
                500                 505                 510

Asp His Glu Thr Tyr Ile Leu Asn Leu Thr Gln Ala Asn Ile Pro Gly
            515                 520                 525

Ala Ile Pro His Trp Gln Leu Leu Tyr Arg Ala Arg Glu Thr Tyr Gly
        530                 535                 540

Leu Pro Asn Thr Leu Pro Thr Ala Trp His Asn Leu Val Tyr Arg Met
545                 550                 555                 560

Arg Gly Asp Met Gln Leu Phe Gln Thr Phe Trp Phe Leu Tyr His Lys
                565                 570                 575

Gly His Pro Pro Ser Glu Pro Cys Gly Thr Pro Cys Arg Leu Ala Thr
                580                 585                 590

Leu Cys Ala Gln Leu Ser Ala Arg Ala Asp Ser Pro Ala Leu Cys Arg
            595                 600                 605

His Leu Met Pro Asp Gly Ser Leu Pro Glu Ala Gln Ser Leu Trp Pro
610                 615                 620
```

```
Arg Pro Leu Phe Cys
625

<210> SEQ ID NO 4
<211> LENGTH: 628
<212> TYPE: PRT
<213> ORGANISM: Homo sapiens

<400> SEQUENCE: 4

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ser
        35                  40                  45

Asp Ser Arg Val Leu Trp Ala Pro Ala Glu Ala His Pro Leu Ser Pro
    50                  55                  60

Gln Gly His Pro Ala Arg Leu His Arg Ile Val Pro Arg Leu Arg Asp
65                  70                  75                  80

Val Phe Gly Trp Gly Asn Leu Thr Cys Pro Ile Cys Lys Gly Leu Phe
                85                  90                  95

Thr Ala Ile Asn Leu Gly Leu Lys Lys Glu Pro Asn Val Ala Arg Val
            100                 105                 110

Gly Ser Val Ala Ile Lys Leu Cys Asn Leu Leu Lys Ile Ala Pro Pro
        115                 120                 125

Ala Val Cys Gln Ser Ile Val His Leu Phe Glu Asp Asp Met Val Glu
    130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Ser Pro Pro
            180                 185                 190

Ala Pro Gly Ala Pro Val Ser Arg Ile Leu Phe Leu Thr Asp Leu His
        195                 200                 205

Trp Asp His Asp Tyr Leu Glu Gly Thr Asp Pro Asp Cys Ala Asp Pro
    210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                245                 250                 255

Leu Glu Ser Leu Leu Ser Gly Leu Gly Pro Ala Gly Pro Phe Asp Met
            260                 265                 270

Val Tyr Trp Thr Gly Asp Ile Pro Ala His Asp Val Trp His Gln Thr
        275                 280                 285

Arg Gln Asp Gln Leu Arg Ala Leu Thr Thr Val Thr Ala Leu Val Arg
    290                 295                 300

Lys Phe Leu Gly Pro Val Pro Val Tyr Pro Ala Val Gly Asn His Glu
305                 310                 315                 320

Ser Ile Pro Val Asn Ser Phe Pro Pro Phe Ile Glu Gly Asn His
                325                 330                 335

Ser Ser Arg Trp Leu Tyr Glu Ala Met Ala Lys Ala Trp Glu Pro Trp
            340                 345                 350

Leu Pro Ala Glu Ala Leu Arg Thr Leu Arg Ile Gly Gly Phe Tyr Ala
        355                 360                 365
```

```
Leu Ser Pro Tyr Pro Gly Leu Arg Leu Ile Ser Leu Asn Met Asn Phe
    370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
                405                 410                 415

Gly Asp Lys Val His Ile Ile Gly His Ile Pro Pro Gly His Cys Leu
            420                 425                 430

Lys Ser Trp Ser Trp Asn Tyr Tyr Arg Ile Val Ala Arg Tyr Glu Asn
            435                 440                 445

Thr Leu Ala Ala Gln Phe Phe Gly His Thr His Val Asp Glu Phe Glu
    450                 455                 460

Val Phe Tyr Asp Glu Glu Thr Leu Ser Arg Pro Leu Ala Val Ala Phe
465                 470                 475                 480

Leu Ala Pro Ser Ala Thr Thr Tyr Ile Gly Leu Asn Pro Gly Tyr Arg
                485                 490                 495

Val Tyr Gln Ile Asp Gly Asn Tyr Ser Arg Ser Ser His Val Val Leu
            500                 505                 510

Asp His Glu Thr Tyr Ile Leu Asn Leu Thr Gln Ala Asn Ile Pro Gly
        515                 520                 525

Ala Ile Pro His Trp Gln Leu Leu Tyr Arg Ala Arg Glu Thr Tyr Gly
    530                 535                 540

Leu Pro Asn Thr Leu Pro Thr Ala Trp His Asn Leu Val Tyr Arg Met
545                 550                 555                 560

Arg Gly Asp Met Gln Leu Phe Gln Thr Phe Trp Phe Leu Tyr His Lys
                565                 570                 575

Gly His Pro Pro Ser Glu Pro Cys Gly Thr Pro Cys Arg Leu Ala Thr
            580                 585                 590

Leu Cys Ala Gln Leu Ser Ala Arg Ala Asp Ser Pro Ala Leu Cys His
        595                 600                 605

Leu Met Pro Asp Gly Ser Leu Pro Glu Ala Gln Ser Leu Trp Pro Arg
    610                 615                 620

Pro Leu Phe Cys
625
```

CHAPERONE-BASED THERAPY FOR NIEMANN-PICK DISEASE

This application claims priority from U.S. Provisional Patent Application Ser. No. 60/525,497, filed Nov. 25, 2003, the disclosure of which is herein incorporated by reference in its entirety.

GOVERNMENT SUPPORT

This work was supported in part by NIH Grant No. HD 28607. Pursuant to the terms of that grant, the federal government may have certain rights to this invention.

FIELD OF THE INVENTION

The present invention provides a method for treating individuals affected with the acid sphingomyelinase-deficient forms of Niemann-Pick disease (i.e., Type A or Type B Niemann-Pick) by administering small molecules as specific molecular "chaperones" for the deficient acid sphingomyelinase (ASM) enzyme associated with the disease.

BACKGROUND OF THE INVENTION

Types A and B Niemann-Pick disease (NPD) are lysosomal storage disorders (LSDs) resulting from the deficient activity of acid sphingomyelinase (ASM), and the subsequent accumulation of sphingomyelin, cholesterol, and other lipids within cells and tissues of affected individuals (Schuchman and Desnick, Niemann-Pick disease types A and B: acid sphingomyelinase deficiencies. In: *The metabolic and molecular bases of inherited disease*. Edited by Schriver C R, Beaudet A L, Valle D, Sly W S; New York. McGraw Hill Inc 3589-3610 2001). Patients with Type A NPD are usually diagnosed early in infancy with organomegaly and follow a rapid, neurodegenerative course that leads to death by about three years of age. In contrast, patients with Type B NPD have little or no central nervous system involvement and often survive into adulthood. However, the Type B form of NPD is clinically heterogeneous and can present with a variety of findings that may include hepatosplenomegaly, growth retardation, frequent respiratory infections, fatigue, and hematologic abnormalities such as high LDL cholesterol and triglycerides, low HDL cholesterol, and low platelets. In addition, several Type B NPD patients have been reported with an intermediate phenotype that involved neurodegeneration (Elleder and Cihula, Eur J Pediatr 1983; 140:323-328; Elleder et al., J Inherit Metab Dis 1986; 9:357-366).

Both forms of NPD are panethnic, although most reported Type A NPD cases occurred among Ashkenazi Jewish individuals. Type B NPD, by contrast, appears to be more prevalent in North African, Arab, and Turkish populations. To date, over 70 mutations in the ASM gene have been reported causing Types A or B NPD (Simonaro et al., Am J Hum Gen. 2002; 71:1413-1419). Among these are a small number of common mutations that predict specific phenotypes. For example, the delta R608 mutation, wherein an arginine at residue 608 (AR608) is deleted, is found in about 10-15% of all NPD patients in North American and Western Europe, and is always associated with a non-neurological form of the disease (i.e., Type B NPD) (Levran et al., J Clin Invest. 1991; 88:806-810). This mutation also is found in about 90% of Type B NPD patients from North Africa (Vanier et al., Hum Genet. 1993; 92:325-330). In contrast to the AR608 mutation, three additional mutations, L302P, where proline replaces leucine at amino acid residue 302, R496L, where leucine replaces arginine at amino acid residue 496, and fsP330, where a premature stop codon is introduced downstream of a proline at amino acid residue 330, account for more than 90% of Type A NPD patients in the Ashkenazi Jewish population (Levran et al., Proc Natl Acad Sci USA. 1991; 88:3748-3752; Levran et al., Blood. 1992; 80:2081-2087; Levran et al., Hum Mut. 1993; 2:317-319). The carrier frequency for these three mutations within the Ashkenazi Jewish community is about 1:80 to 1:100 (Li et al. Am J Hum Genet. 1997; 61 (suppl): A24).

Recently, three isoforms of the human ASM gene were cloned and several mutations were identified that can reliably be used in diagnostic evaluations of obligate heterozygotes for NPD Types A and B in the Ashkenazi Jewish population (see U.S. Pat. Nos. 5,773,278 and 5,686,240 to Schuchman et al.).

Supportive management is the only treatment available for most LSD patients. Enzyme replacement therapy (ERT) has been developed or is currently under development for several LSDs, including Gaucher disease, Fabry disease, and mucopolysaccharidosis Type I (MPS I) (Desnick and Schuchman, Nat Rev Genet. 2002; 3:954-966), but since the enzymes do not cross the blood brain barrier after intravenous infusion, this is not a useful strategy for patients with severe neurological involvement (e.g., Type A NPD). Substrate deprivation therapy, which uses small molecule inhibitors to prevent the synthesis of pathogenic substrates, also has been developed or is under evaluation for several LSDs, and has conditional marketing approval in Europe and the United States for Gaucher disease (Butters et al., Philos Trans R Soc Lond B Biol Sci. 2003; 358:927-945.). One advantage of this approach as compared to ERT is that the small molecule inhibitors may potentially cross the blood brain barrier and prevent substrate accumulation in the brain.

Another small molecule approach recently developed is known as chemical chaperone, or active site-specific chaperone (ASSC) therapy (Fan et al Nat Med. 1999; 5: 112-115; Fan, Trends Pharmacol Sci. 2003; 24: 355-360). ASSC uses low concentrations of potent enzyme inhibitors to enhance the folding and activity of mutant proteins in specific LSDs. This approach was first evaluated in Fabry disease, where a small molecule inhibitor of alpha-galactosidase A, 1-deoxygalactononjirimycin (DGJ), was used to enhance the residual alpha-galactosidase activity in cell lines from Fabry disease patients (see U.S. Pat. No. 6,274,597 to Fan et al.). U.S. Pat. No. 6,583,158, to Fan et al. further exemplifies the ASSC strategy for numerous other lysosomal storage diseases, including Gaucher disease and $G_{M1}$-gangliosidosis, and demonstrates that this therapeutic strategy of using potent competitive inhibitors as chemical chaperones to enhance the residual enzyme activity in a patient's cells is not limited to patients with Fabry disease, but can be applied to numerous enzyme deficiency diseases, particularly LSDs.

ASSC therapy is now currently under development for several LSDs, including Gaucher disease, and offers several advantages over ERT or substrate deprivation therapy. Most notably, since the active site inhibitors used in ASSC are specific for the disease-causing enzyme, the therapy is targeted to a single protein and metabolic pathway, unlike substrate deprivation therapy that inhibits an entire synthetic pathway. Like substrate deprivation therapy, the small molecule inhibitors for ASSC have the potential of crossing the blood brain barrier and could be used to treat neurological LSD forms.

In addition to enhancing the activity of the deficient enzymes associated with the LSDs, the ASSCs have also been demonstrated to enhance the activity of the corresponding wild-type enzyme (see U.S. Pat. No. 6,589,964 to Fan et al.), thus having utility as co-therapy for enzyme replacement therapy in LSD patients.

Type A NPD is an important candidate for ASSC. First, all patients with Type A NPD develop a severe, neurological phenotype that leads to death by about three years of age. There is currently no treatment for the neurological features of this disorder. However, studies using an ASM knock-out mouse model have shown that enhancing the residual ASM activity up to about 5% of normal activity can completely prevent the occurrence of brain disease and lead to a normal lifespan, suggesting that a low level of functional ASM prevents neurodegeneration in Type A NPD patients (Marthe et al., Hum Mol Genet. 2000; 9: 1967-1976). In addition, two of these three mutations (L302P and R496L) that are responsible for most Ashkenazi Jewish Type A NPD patients are point mutations that might be amenable to ASSC. In addition, about 15% of Type B NPD patients worldwide carry at least one copy of the ΔR608 mutation. Thus, there is a substantial need for this form of small molecule therapy.

SUMMARY OF THE INVENTION

The present invention provides a method of treating patients having Type A or B NPD by administering small molecule ceramide analogues, or phospho-containing sphingomyelin or nucleotide analogues, as active site-specific chaperones (ASSC).

In one embodiment, the ASSC is administered to individuals having the L302P mutation in the human acid sphingomyelinase (ASM) gene.

In another embodiment, the ASSC is administered to individuals having the R496L mutation in the human acid sphingomyelinase (ASM) gene.

In another embodiment, the ASSC is administered to individuals having the delta R608 mutation.

In another embodiment, the small molecule is a sphingomyelin analogue having the formula:

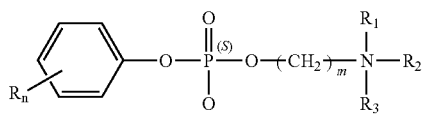

wherein each R if present, is independently optionally substituted $C_{1-10}$ alkyl, halo, $NO_2$, CN, OH, $C_{1-6}$ alkoxy; $R_1$, $R_2$, and $R_3$ are independently H, $C_{1-10}$ alkyl, aryl or aralkyl; n is 0-5, and m is 1-3, preferably 2.

In another embodiment, the small molecule is a sphingomyelin analogue having the formula:

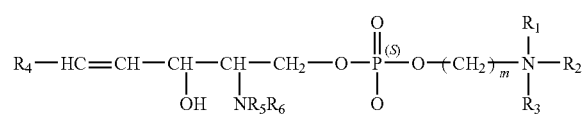

wherein $R_1$, $R_2$, $R_3$ and m are as defined above, $R_4$ is $C_{10-20}$ alkyl, $R_5$ and $R_6$ are independently H, $C_{1-10}$ alkyl, aryl or aralkyl.

In a preferred embodiment, the sphingomyelin analogue has the following structure:

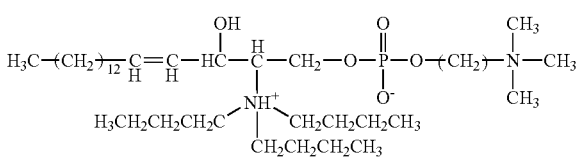

In yet another embodiment, the small molecule is a ceramide analogue having a formula:

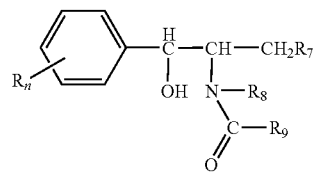

wherein $R_n$ is as defined above, $R_7$ is H or OH, $R_8$ is H, $C_{1-10}$ alkyl, aryl or aralkyl, and $R_9$ is $C_{10-20}$ alkyl.

In a specific embodiment, the ASSC is D-MAPP (see FIG. 1).

In still another embodiment, the small molecule analogue is a phosphonucleotide analogue, such as the following:

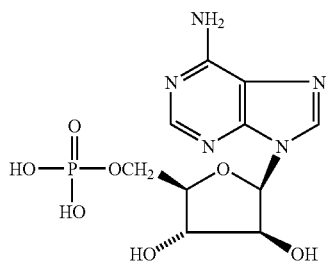

However, other phosphonucleotides such as but not limited to adenosine monophosphate, cytosine monophosphate, and adenosine diphosphate are also contemplated.

In one embodiment, the small molecule analogue can be administered as monotherapy.

In another embodiment, the small molecule analogue can be administered in conjunction with wild-type, recombinant ASM as enzyme replacement therapy. Stability and, hence, activity of the endogenous ASM protein will be enhanced concurrently with the increased stability of the administered replacement functional ASM protein.

In yet another embodiment, the small molecule analogue is administered in conjunction with a recombinant vector encoding a functional ASM, i.e., with gene therapy.

The invention further provides a method for increasing the production of recombinant ASM protein by non-mammalian host cells by contacting the host cell in a medium comprising a small molecule analogue of the present invention.

The invention also provides compositions comprising the small molecule analogue and a pharmaceutically acceptable carrier.

The invention further provides compositions comprising a purified ASM protein and a small molecule analogue chaperone as described herein in a pharmaceutically acceptable carrier.

Also provided by the present invention is a method of preventing or treating a subject having been diagnosed with, or genetically pre-disposed to developing, NPD by administering a small molecule analogue, alone or in combination with enzyme replacement or gene therapy.

BRIEF DESCRIPTION OF THE DRAWINGS

FIGS. 2A-D. FIG. 2A depicts the structure of the ceramide analogues that can be used in the present invention, while FIGS. 2B and 2C depict the structures of the sphingomyelin analogues that can be used to practice the present invention. FIG. 2D depicts the structure of a preferred embodiment of a sphingomyelin analogue that is a candidate for an NPD ASCC.

DETAILED DESCRIPTION

Figure 1:
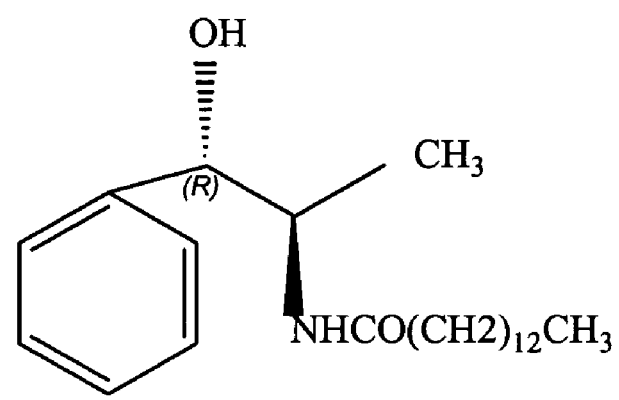
FIG. 1 depicts the structure of D-MAPP, one preferred ASSC of the invention.
Figure 3:
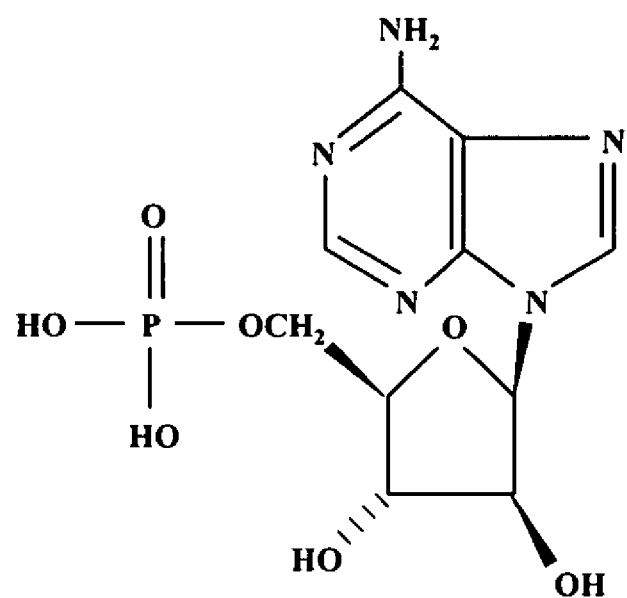
FIG. 3 shows the structure of a nucleotide analogue that is an inhibitor and ASSC of ASM.

The present invention is based, in part, on the use of ceramide, sphingomyelin or phosphonucleotide analogues as NPD ASSCs. When cultured skin fibroblasts from a patient with Type A NPD containing two copies of the R496L mutation were incubated in the presence of D-MAPP (5-50 micromolar), for three days, the residual ASM activity was enhanced up to 3-fold, or to about 3% of normal (from a starting activity of less than 1% of normal-see FIG. 5). Similarly, when a spingomyelin analogue was cultured with normal fibroblasts (20 micomolar) for 5 days, inhibited normal ASM activity by 90%, suggesting that it is an effective chaperone for ASM.

In contrast to the ASSCs that have been described previously by Fan et al., (U.S. Pat. Nos. 6,274,597; 6,583,158; 6,589,964; and 6,599,919), which are imino sugar analogues of glucose and galactose that are known glycosidase inhibitors, the small molecule analogs described of the present invention are not imino sugars. The present compounds inhibit ASM at concentrations ranging from about 50-100 µM. This is also contrary to what has been described by Hannun et al. in U.S. Pat. No. 5,830,916, which discloses the use of one of the ceramide analogues described herein, D-MAPP, as an alkaline ceramidase inhibitor, to increase the accumulation of ceramide by inhibiting ceramidase. Ceramidase is an enzyme which catalyzes the hydrolysis of ceramide into sphingosine and a fatty acid. Hannun also discloses that D-MAPP has no effect on endogenous levels of sphingomyelin, arguing against an effect on sphingomyelinase (the enzyme which degrades sphingomyelin) in whole cells. A similar lack of effect was seen with β-glucosidase, a glycosidase enzyme which catalyzes the hydrolysis of aryl and alkyl beta-D-glucosides in vitro (using whole cells).

Compounds that are inhibitors of various lipid-related enzymes are also described in U.S. published patent application 2003/0133004 to Dagan et al. This application describes several compounds that modify the synthesis or metabolism of sphingolipids. In particular, sphingomyelin analogues are described which inhibit synthesis of sphingomyelin, thereby increasing concentrations of ceramide in the cells, leading to apoptosis. The application also refers to treating glycolipid storage disorders using these inhibitors, by inhibition of sphingomyelin, the pathologic lipid that accumulates in some LSDs such as NPD. This is an example of substrate deprivation or reduction. One compound described in the application is shown to inhibit acidic and neutral sphingomyelinases.

DEFINITIONS

As used herein, the term "active site-specific chaperone" (ASSC) refers to any molecule including a protein, peptide, nucleic acid, carbohydrate, etc. that specifically interacts reversibly with an active site of a protein and enhances formation of a stable molecular conformation. As used herein, "active site-specific chaperone" does not include endogenous general chaperones present in the ER of cells such as Bip, calnexin or calreticulin, or general, non-specific chemical chaperones such as deuterated water, DMSO, or TMAO. According to the present invention, the ASSC is a ceramide, sphingomyelin or nucleotide analogue and the protein with which it interacts is ASM.

Acid sphingomylinase, or ASM, has a nucleotide and amino acid sequence as described in U.S. Pat. No. 6,541,218. The ASM amino acid sequence is described infra in SEQ ID NO: 1. This term also includes species orthologs and variants of ASM.

As used herein, the term "active site" refers to the region of a protein that binds a substrate or binding partner and contributes the amino acid residues that directly participate in the making and breaking of chemical bonds. According to the present invention, the active site encompasses the catalytic domain of the ASM enzyme.

D-MAPP refers to D-erythro-2-(N-myristoylamino)-1-phenyl-1-propanol. D-MAPP is further described in U.S. Pat. No. 5,369,030 and is depicted in FIG. 1, herein.

The term "stabilize a proper conformation" refers to the ability of a compound of the invention to induce a conformation of a mutated ASM protein in a way that is functionally identical to the conformation of the wild-type ASM protein. The term "functionally identical," means that there may be minor variations in the conformation (indeed almost all proteins exhibit some conformational flexibility in their physiological state) but that conformational flexibility does not result in (1) protein aggregation, (2) elimination through the endoplasmic reticulum-associated degradation pathway, (3) impairment of ASM function, and/or (4) improper transport within the cell. This term also refers to the stabilization of a wild-type or functional ASM, such as ASM that is produced for ERT.

The term "wild-type activity" refers to the normal physiological function of ASM in a cell. Such functionality can be tested by any means known to establish functionality of a protein. Certain tests may evaluate attributes ASM that may or may not correspond to its actual in vivo function, but nevertheless are aggregate surrogates of protein functionality, and wild-type behavior in such tests is an acceptable consequence of the protein folding rescue techniques of the invention. One such activity in accordance with the invention is appropriate transport of ASM from the endoplasmic reticulum to the lysosome.

The term "functional ASM protein" refers to an ASM protein that has the ability to fold in a proper conformation, achieve its native location in the cell, and have catabolic activity towards sphingomyelin and other lipid substrates. A functional ASM protein includes wild-type ASM proteins (see definitions below), e.g., as depicted in SEQ ID NO: 1, and ASM proteins having wild-type activity.

The term "enhancing the activity" of ASM means stabilizing a proper conformation of a mutant ASM protein so that it becomes a functional ASM protein (i.e., folds in a proper conformation, achieves its native location in the cell, and has catabolic activity towards sphingomyelin and other lipid substrates). This term also refers to increasing the wild-type activity of exogenously administered ASM protein, i.e., by increasing the stability and extending the half-life of wild-type ASM, thus, prolonging its activity.

The term "inhibitor of ASM" refers to a compound that exhibits greater selectivity for inhibiting ASM over other enzymes, including enzymes involved in the synthesis of sphingomyelin, at a concentration that is below a pharmacologic dose. The inhibitor must inhibit ASM specifically. As used herein, inhibitors do not include compounds that may bind in the active site, but do not have inhibitory activity per se except at extremely high concentrations that are not conducive to administering to individuals.

The term "concentration below that required to inhibit ASM" refers to the concentration of the compounds of the present invention that enhances ASM activity without inhibiting its activity. According to the present invention, this concentration will be in a range from about 5-50 µM.

As used herein the term "mutant ASM protein" refers to an ASM translated from a gene containing a genetic mutation(s) that results in an altered protein sequence that does not achieve a native conformation under the conditions normally present in the ER. The failure to achieve this conformation results in the ASM being degraded, rather than being transported through a normal pathway in the protein transport system to the lysosomes.

In one embodiment, the ASM mutation rescued by the method of the present invention is R496L (SEQ ID NO: 2), a G to T transversion mutation at codon nucleotide 1487. It is not yet known whether the substitution of the basic arginine for the more hydrophobic leucine residue alters the enzyme catalytic activity, enzyme stability, or both.

In another specific embodiment, the ASM mutation rescued by the present method is a T to C transition of nucleotide 905, which results in the substitution of a proline for a leucine (L302P-SEQ ID NO: 3).

In yet another specific embodiment, the ASM mutation rescued by the ASSC of the present method is a deletion mutation of R608 (AR608-SEQ ID NO: 4).

Molecular Biology Definitions

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization*; B. D. Hames & S. J. Higgins eds. (1985); *Transcription And Translation*; [B. D. Hames & S. J. Higgins, eds. (1984); *Animal Cell Culture*; R. I. Freshney, ed. (1986); *Immobilized Cells And Enzymes*; IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994).

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein, may be associated with other proteins or nucleic acids, or both, with which it associates in the cell, or with cellular membranes if it is a membrane-associated protein. In a specific embodiment, an isolated ASM protein is a recombinant ASM protein expressed from an expression vector. An isolated material may be, but need not be, purified.

The term "purified" as used herein refers to material that has been isolated under conditions that reduce or eliminate unrelated materials, i.e., contaminants. For example, a purified ASM protein is preferably substantially free of other proteins or nucleic acids with which ASM is normally associated in a cell. As used herein, the term "substantially free" is used operationally, in the context of analytical testing of the material. Preferably, purified ASM substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

The term "host cell" means any cell of any organism that is selected, modified, transformed, grown, or used or manipulated in any way, for the production of a substance by the cell, for example the expression by the cell of a human ASM gene, including a DNA or RNA sequence, or the ASM enzyme. Host cells can further be used for preliminary evaluation of the ASSC concept other assays. A "recombinant DNA molecule" is a DNA molecule that has undergone a molecular biological manipulation or engineering. In one embodiment of the invention, the host cell is a fibroblast.

A "gene" is a sequence of nucleoides which code for a "gene product". Generally, a gene product is a protein. However, a gene product can also be another type of molecule in a cell, such as an RNA (e.g., a tRNA or a rRNA). For the purposes of the present invention, a gene product also refers to an mRNA sequence which may be found in a cell. As used herein, a gene refers to the nucleotide sequences encoding wild-type or mutant ASM.

A "wild-type ASM gene" refers to nucleic acid sequences which encode an ASM protein capable of having functional biological activity in vivo. The wild-type ASM nucleic acid sequence may contain nucleotide changes that differ from the known, published sequence, e.g., in U.S. Pat. No. 6,541,218, as long as the changes result in amino acid substitutions that have little or no effect on the biological activity. As used herein, the term wild-type may also include ASM nucleic acid sequences engineered to encoding an ASM protein capable of increased or enhanced activity relative to the endogenous or native ASM protein.

A "wild-type ASM protein" refers to any protein encoded by a wild-type gene that is capable of having functional biological activity when expressed or introduced in vivo. Such functionality can be tested by any means known to establish functionality of a protein.

The term "express" and "expression" means allowing or causing the information in an ASM gene or DNA sequence to become manifest, for example producing RNA (such as rRNA or mRNA) or an ASM protein by activating the cellular functions involved in transcription and translation of a corresponding ASM gene or DNA sequence, i.e., sequences encoding ASM. An ASM DNA sequence is expressed by a cell to form an "expression product" such as an ASM RNA (e.g., a mRNA or a rRNA) or an ASM protein. The expression product itself, e.g., the resulting ASM RNA or protein, may also said to be "expressed" by the cell.

The term "transfection" or "transformation" means the introduction of a "foreign", i.e., extrinsic or extracellular gene, DNA or RNA sequence into a host cell so that the host cell will express the introduced gene or sequence to produce a desired substance. In this invention, the substance is typically an RNA coded by the introduced gene or sequence, and an enzyme protein coded by the introduced gene or sequence. The introduced gene or sequence may also be called a "cloned" or "foreign" gene or sequence, may include regulatory or control sequences (e.g., start, stop, promoter, signal, secretion or other sequences used by a cell's genetic machinery). The gene or sequence may include nonfunctional sequences or sequences with no known function. A host cell that receives and expresses introduced DNA or RNA has been "transformed" or "transfected" and is a "transformant" or a "clone". The DNA or RNA introduced to a host cell can come from any source, including cells of the same genus or species as the host cell or cells of a different genus or species. As used herein, transfection or transformation will include introduction of sequences encoding functional ASM in individuals having mutated endogenous ASM genes.

The terms "vector", "cloning vector", and "expression vector" mean the vehicle by which an ASM DNA or RNA sequence (e.g., a foreign gene) can be introduced into a host cell so as to transform the host and promote expression (e.g., transcription and translation) of the introduced sequence. Vectors include any genetic element, such as a plasmid, phage, transposon, cosmid, chromosome, virus, virion, etc., which is capable of replication when associated with the proper control elements and which can transfer ASM gene sequences between cells. Thus, the term includes cloning and expression vehicles, as well as viral vectors.

The term "expression system" means a host cell and compatible vector under suitable conditions, e.g. for the expression of an ASM protein coded for by foreign DNA carried by the vector and introduced to the host cell. Common expression systems include E. coli host cells and plasmid vectors, insect host cells such as Sf9, Hi5 or S2 cells and Baculovirus vectors, and expression systems, and mammalian host cells and vectors.

The term "gene therapy" refers to a method of changing the expression of an endogenous gene by exogenous administration of a gene, i.e., an ASM gene. As used herein, gene therapy also refers to the replacement of defective ASM gene, or replacement of a missing ASM gene, by introducing a functional gene or portion of a gene corresponding to the defective or missing ASM gene into somatic or stem cells of an individual in need. Gene therapy can be accomplished by "ex vivo" methods, in which differentiated or somatic stem cells are removed from the individual's body followed by the introduction of a normal copy of the defective gene into the explanted cells using a viral vector as the gene delivery vehicle. In addition, in vivo transfer is direct gene transfer into cells in the individual in situ using a broad range of viral vectors, liposomes, protein DNA complexes or naked DNA in order to achieve a therapeutic outcome.

The term "recombinant protein" refers to an ASM protein (gene product) encoded by a therapeutic ASM gene carried on a vector. Generally, the cell receiving the vector will lack expression and/or activity of any endogenous ASM protein corresponding to the recombinant protein, or if there is expression of such an endogenous ASM protein, it is of a mutant or at a very low level. In one embodiment, the recombinant protein is produced by a cell in tissue culture for experimental and therapeutic purposes. In another embodiment, the recombinant protein is produced in vivo from cells transformed with vector, wherein the vector or the cells comprising the vector have been administered to a subject, i.e., gene therapy. The recombinant ASM protein will likely be indistinguishable from wild-type protein in normal individuals, i.e., individuals who are not deficient in the protein.

Therapeutic Applications

The present invention further provides a method for the prevention or treatment of Type A and Type B NPD, which method comprises increasing the expression or activity of the mutant ASM enzyme, or by increasing the activity of recombinant, wild-type replacement ASM enzyme, in a subject or patient in need of such treatment.

A "subject" or "patient" is a human or an animal that has developed, or is likely to develop NPD, more particularly a mammal, preferably a rodent or a primate, and most preferably a human. In one embodiment, the patient is a member of the Ashkenazi Jewish population who has been diagnosed with, or who has been identified as having an increased risk of developing NPD due inherited mutations in the ASM gene. In another embodiment, the patient is a member of the French Canadian population of Nova Scotia, an inhabitant of the Maghreb region (Tunisia, Morocco, Algeria) of North Africa (Type B), or a member of the Spanish-American population of southern New Mexico and Colorado. However, Niemann-Pick disease is pan-ethnic, and the term subject encompasses anyone in the world having, or genetically at risk of developing, NPD.

The term "prevention" refers to the prevention of the onset of the disease, which means to prophylactically interfere with a pathological mechanism that results in the disease. In the context of the present invention, such a pathological mechanism can be an increase in mutant protein folding and expression of ASM.

The term "treatment" means to therapeutically intervene in the development of a disease in a subject showing a symptom of this disease. In the context of the present invention, these symptoms can include but are not limited to, e.g., the accumulation of sphingomyelin in reticuloendothelial lysosomes, which results in hepatosplenomegaly, psychomotor retardation, pulmonary abnormalities, progressive neurodegeneration. In some instances, treatment will prevent death resulting from NPD.

The term "therapeutically effective amount" is used herein to mean an amount or dose of ASSC (i.e., sphingomyelin, ceramide or nucleotide analogues) sufficient to increase the level of mutant ASM expression, e.g., to about 3-5%, preferably by about 10%, and more preferably by about 30% of the level found in normal cells. Preferably, a therapeutically effective amount can ameliorate or prevent a clinically significant deficit in ASM activity in the subject. Alternatively, a therapeutically effective amount is sufficient to cause an improvement in a clinically significant condition in the subject, e.g., amelioration of progressive neurodegeneration in Type B NPD patients.

According to the present invention, a "therapeutically effective amount" also means an amount of the small molecule analogue that enhances without inhibiting the activity of the ASM protein, i.e., an effective amount enhances more than it inhibits so the net effect is an enhancement. This will generally fall somewhere below the $IC_{50}$ value of that inhibitor for ASM, or below about 50 µM.

The small molecule analogue that increases mutant ASM expression or activity is advantageously formulated in a pharmaceutical composition, with a pharmaceutically acceptable carrier. In this context, the small molecule analogue is the active ingredient or therapeutic agent.

The concentration or amount of the active ingredient depends on the desired dosage and administration regimen, as discussed below. Suitable dose ranges of the small molecule analogue may include from about 1 mg/kg to about 100 mg/kg of body weight per day.

Combination Therapy

ASSC and protein replacement. The pharmaceutical compositions of the invention may also include other biologically active compounds in addition to the sphingomyelin, ceramide or nucleotide analogue. For example, in one embodiment, the small molecule analogue may be administered in solution with the replacement, wild-type (or otherwise functional) recombinant ASM during enzyme infusion in replacement therapy. Protein replacement therapy increases the amount of protein by exogenously introducing wild-type or biologically functional protein by way of infusion. This therapy has been developed for many genetic disorders including Gaucher disease and Fabry disease. The wild-type enzyme is purified from a recombinant cellular expression system (e.g., mammalian cells or insect cells—see U.S. Pat. Nos. 5,580,757 to Desnick et al.; 6,395,884 and 6,458,574 to Selden et al.; 6,461,609 to Calhoun et al.; 6,210,666 to Miyamura et al.; 6,083,725 to Selden et al.; 6,451,600 to Rasmussen et al.; 5,236,838 to Rasmussen et al.; and 5,879,680 to Ginns et al.), human placenta, or animal milk (see U.S. Pat. No. 6,188,045 to Reuser et al.).

After the infusion, the exogenous ASM enzyme is expected to be taken up by tissues through non-specific or receptor-specific mechanisms. In general, the uptake efficiency is not high, and the circulation time of the exogenous protein is short (Ioannu et al., Am. J. Hum. Genet. 2001; 68: 14-25). In addition, the exogenous ASM is unstable in circulation and subject to rapid intracellular degradation. Accordingly, it is expected that co-administration with small molecule analogue, an ASSC for ASM, will improve the stability and prevent the degradation of the exogenously administered ASM.

In another embodiment, the small molecule analogue also may be administered in conjunction with, but not necessarily in the same composition, as the recombinant, functional ASM protein. In this embodiment, the replacement ASM protein and the small molecule analogue are formulated in separate compositions. The small molecule analogue and the replacement ASM may be administered according to the same route, e.g., intravenous infusion, or different routes, e.g., intravenous infusion for the replacement protein, and oral administration for the ASSC.

ASSC and Gene Therapy. In addition, the small molecule analogue compositions of the present invention may be administered in conjunction with a recombinant vector encoding a wild-type, or otherwise functional ASM gene, i.e., in association with gene therapy. Recently, recombinant gene therapy methods are in clinical or pre-clinical development for the treatment of lysosomal storage disorders, see, e.g., U.S. Pat. No. 5,658,567, for recombinant alpha-galactosidase A therapy for Fabry disease; U.S. Pat. No. 5,580,757, for Cloning and Expression of Biologically Active α-galactosidase A as a Fusion Protein; U.S. Pat. No. 6,066,626, for Compositions and method for treating lysosomal storage disease; U.S. Pat. No. 6,083,725, for Transfected human cells expressing human alpha-galactosidase A protein; U.S. Pat. No. 6,335,011, for Methods for delivering DNA to muscle cells using recombinant adeno-associated virus virions to treat lysosomal storage disease; Bishop, D. F. et al., Proc. Natl. Acad Sci. USA 1986; 83:4859-4863; Medin, J. A. et al., Proc. Natl. Acad. Sci. USA 1996; 93:7917-7922; Novo, F. J., Gene Therapy 1997; 4:488-492; Ohshima, T. et al., Proc. Natl. Acad. Sci. USA 1997; 94:2540-2544; Sugimoto Y. et al., Human Gene Therapy 1995; 6:905-915; Sly et al., Proc. Natl. Acad. Sci. USA 2002; 99(9):5760-2; Raben et al., Curr. Mol. Med 2002; 2(2):145-66; Eto et al., Curr. Mol. Med. 2002; 2(1):83-9; Vogler et al., Pediatr. Dev. Pathol. 2001; 4(5):421-33; Barranger et al., Expert Opin. Biol. Ther. 2001; 1(5):857-67; Yew et al., Curr. Opin. Mol. Ther. 2001; 3(4):399-406; Caillaud et al., Biomed. Pharmacother. 2000; 54(10):505-12 and Ioannu et al., J. Am. Soc. Nephrol. 2000; 11(8):1542-7.

It is important to note that in addition to stabilizing the expressed ASM enzyme, small molecule analogue will also stabilize and enhance expression of any endogenous mutant ASM that is deficient as a result of mutations that prevent proper folding and processing in the ER.

Formulations and Administration

The phrase "pharmaceutically acceptable" refers to molecular entities and compositions that are physiologically tolerable and do not typically produce an allergic or similar untoward reaction, such as gastric upset, dizziness and the like, when administered to most humans. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

According to the invention, the pharmaceutical composition of the invention, e.g., D-MAPP, can be introduced parenterally, transmucosally, e.g., orally (per os), nasally, or rectally, or transdermally. Parental routes include intravenous, intra-arteriole, intramuscular, intradermal, subcutaneous, intraperitoneal, intraventricular, and intracranial administration.

With respect to combination therapy with protein replacement, in the embodiment where the ASSC is administered in the same composition with the replacement ASM enzyme, the formulation is preferably suitable for parenteral administration, including intravenous subcutaneous, and intraperitoneal, however, formulations suitable for other routes of administration such as oral (e.g., encapsulated enzyme), intranasal or transdermal are also contemplated.

In one embodiment, transdermal administration is achieved by liposomes. Lipid bilayer vesicles are closed, fluid-filled microscopic spheres which are formed principally from individual molecules having polar (hydrophilic) and non-polar (lipophilic) portions. The hydrophilic portions may comprise phosphato, glycerylphosphato, carboxy, sulfato, amino, hydroxy, choline or other polar groups. Examples of lipophilic groups are saturated or unsaturated hydrocarbons such as alkyl, alkenyl or other lipid groups. Sterols (e.g., cholesterol) and other pharmaceutically acceptable adjuvants (including anti-oxidants such as alpha-tocopherol) may also be included to improve vesicle stability or confer other desirable characteristics.

Liposomes are a subset of these bilayer vesicles and are comprised principally of phospholipid molecules that contain two hydrophobic tails consisting of fatty acid chains. Upon exposure to water, these molecules spontaneously align to form spherical, bilayer membranes with the lipophilic ends of the molecules in each layer associated in the center of the membrane and the opposing polar ends forming the respective inner and outer surface of the bilayer membrane(s). Thus, each side of the membrane presents a hydrophilic surface while the interior of the membrane comprises a lipophilic medium. These membranes may be arranged in a series of concentric, spherical membranes separated by thin strata of water, in a manner not dissimilar to the layers of an onion, around an internal aqueous space. These multilamellar vesicles (MLV) can be converted into Unilamellar Vesicles (UV) with the application of a shearing force. The advantage of using liposomes to deliver the ceramide and sphyingomyelin analogues according to the method of the present invention is that liposomes may cross the blood-brain barrier. Since NPD Type A is characterized by neurodegeneration due to an accumulation of sphingomyelin, effective targeting to the brain is critical for any therapeutic for Type A.

The pharmaceutical formulations suitable for injectable use include sterile aqueous solutions (where water soluble) or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, sorbic acid, and the like. In many cases, it will be preferable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the purified ASM enzyme and the small molecule analogue in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Preferably the formulation contains an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment. The formulation also preferably contains a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

For lyophilization of ASM enzyme and small molecule ASSC preparations, the enzyme concentration can be 0.1-10 mg/mL. Bulking agents, such as glycine, mannitol, albumin, and dextran, can be added to the lyophilization mixture. In addition, possible cryoprotectants, such as disaccharides, amino acids, and PEG, can be added to the lyophilization mixture. Any of the buffers, excipients, and detergents listed above, can also be added.

Formulations of the small molecule analogue (with or without ASM) for inhalation administration may contain lactose or other excipients, or may be aqueous solutions which may contain polyoxyethylene-9-lauryl ether, glycocholate or deoxycocholate. A preferred inhalation aerosol is characterized by having particles of small mass density and large size. Particles with mass densities less than 0.4 gram per cubic centimeter and mean diameters exceeding 5 μm efficiently deliver inhaled therapeutics into the systemic circulation. Such particles are inspired deep into the lungs and escape the lungs' natural clearance mechanisms until the inhaled particles deliver their therapeutic payload (Edwards et al., Science. 1997; 276:1868-1872). Replacement protein preparations of the present invention can be administered in aerosolized form, for example by using methods of preparation and formulations as described in, U.S. Pat. Nos. 5,654,007, 5,780,014, and 5,814,607, each incorporated herein by reference. Formulation for intranasal administration may include oily solutions for administration in the form of nasal drops, or as a gel to be applied intranasally.

Formulations for topical administration of the small molecule analogue to the skin surface may be prepared by dispersing the composition with a dermatological acceptable carrier such as a lotion, cream, ointment, or soap. Particularly useful are carriers capable of forming a film or layer over the skin to localize application and inhibit removal. For topical administration to internal tissue surfaces, the composition may be dispersed in a liquid tissue adhesive or other substance known to enhance adsorption to a tissue surface. Alternatively, tissue-coating solutions, such as pectin-containing formulations may be used.

In preferred embodiments, the formulations of the invention are supplied in either liquid or powdered formulations in devices which conveniently administer a predetermined dose of the preparation; examples of such devices include a needleless injector for either subcutaneous or intramuscular injection, and a metered aerosol delivery device. In other instances, the preparation may be supplied in a form suitable for sustained release, such as in a patch or dressing to be applied to the skin for transdermal administration, or via erodable devices for transmucosal administration. In instances where the formulation, e.g., the D-MAPP or other small molecule analogue is orally administered in tablet or capsule form, the preparation might be supplied in a bottle with a removable cover or as blister packs.

In the embodiment where the small molecule analogue is administered separately, or the ASSC is administered alone as monotherapy, the small molecule analogue can be in a form suitable for any route of administration, including but not limited to all of the forms described above, e.g., as sterile aqueous solution, nasal inhalation, transdermal, or in a dry lyophilized powder to be added to the formulation of the replacement protein during or immediately after reconstitution to prevent aggregation in vitro prior to administration. Alternatively, in a preferred embodiment, the small molecule analogue can be formulated for oral administration in the form of tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art.

Liquid preparations for oral administration of the small molecule analogue may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

With respect to combination therapy with gene therapy (or as monotherapy) the small molecule analogue ASSCs may be separately formulated for administration by e.g., oral, parenteral, transdermal, or transmucosal routes, including but not limited to those described above. In a preferred embodiment, the small molecule analogue is administered orally, as a tablet or capsule or capsules prepared by conventional means with pharmaceutically acceptable excipients, such as described above. Alternatively, the small molecule analogue may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. In another embodiment, the small molecule analogue may be in powder form for constitution with a suitable vehicle, e.g., sterile pyrogen-free water, before use.

The small molecule analogue, may also be formulated in rectal compositions such as suppositories or retention enemas, e.g., containing conventional suppository bases such as cocoa butter or other glycerides.

In addition to the formulations described above, the small molecule analogue may also be formulated as a depot preparation. Such long acting formulations may be administered by implantation (for example subcutaneously or intramuscularly) or by intramuscular injection. Thus, for example, the small molecule analogue may be formulated with suitable polymeric or hydrophobic materials (for example as an emulsion in an acceptable oil) or ion exchange resins, or as sparingly soluble derivatives, for example, as a sparingly soluble salt.

Timing. When the replacement ASM protein and small molecule analogue are in separate formulations, administration may be simultaneous, or the small molecule analogue may be administered prior to, or after the ASM replacement protein. For example, where the ASM replacement protein is administered intravenously, the small molecule analogue may be administered during a period from 0 h to 6 h later. Alternatively, the small molecule analogue may be administered from 0 to 6 h prior to the protein.

In a preferred embodiment, where the small molecule analogue and replacement protein are administered separately, and where the has a short circulating half-life (e.g., small molecule), the small molecule analogue may be orally administered continuously, such as daily, in order to maintain a constant level in the circulation. Such constant level will be one that has been determined to be non-toxic to the patient, and optimal regarding interaction with a target replacement protein during the time of administration to confer a non-inhibitory, therapeutic effect.

In another embodiment, the small molecule analogue is administered during the time period required for turnover of the replacement ASM protein (which will be extended by administration of the small molecule analogue).

Regardless of the timing, the administration must be such that the concentrations of the ASM protein and small molecule analogue must be such that the small molecule analogue stabilizes, but does not prevent or inhibit the protein's activity in vivo. This also applies where the replacement ASM protein and small molecule analogue are administered in the same formulation.

With respect to the timing of the small molecule analogue and gene therapy combination therapy, administration of the small molecule analogue according to the present invention will generally follow delivery of the ASM gene, to allow for expression of the recombinant ASM enzyme by the target cells/tissue. Since the expression of the ASM gene will be sustained for a period of time, for as long as the gene is expressible, the small molecule analogue will be remained effective as a chaperone and stabilizer for the recombinant ASM enzyme. Therefore, administration of the small molecule analogue will be necessary for the same period as the gene is expressed.

In a preferred embodiment, since the small molecule analogue has a short circulating half-life, it is preferred that the small molecule analogue will be orally administered frequently, such as daily, in order to maintain a constant level in the circulation. Such a constant level will be one that has been determined to be non-toxic to the patient, and optimal regarding interaction with the protein, which will be continuously produced, to confer a non-inhibitory, therapeutic effect.

According to the present invention, since that the therapeutic ASM gene supplements inadequate activity of an endogenous mutant ASM gene, the timing of the small molecule analogue delivery becomes less significant since the effective amount can enhance the activity of the endogenous mutant ASM as well as increase the efficiency of the therapeutic ASM gene product.

The presence of an ASSC, e.g., D-MAPP, for the ASM enzyme encoded by the administered ASM gene will have the benefit of improving the efficiency of protein processing during synthesis in the ER (i.e., by preventing aggregation), and prolonging in the circulation and tissue the half-life of the ASM enzyme, thereby maintaining effective levels over longer time periods. This will result in increased expression in clinically affected tissues. This confers such beneficial effects to the NPD patient as enhanced relief, reduction in the frequency of treatment, and/or reduction in the amount of ASM gene administered. This will also reduce the cost of treatment.

Gene Therapy. The ASM nucleic acids used for combination therapy with the ASSCs invention may be administered by any known methods, including methods used for gene therapy that are available in the art. The identified and isolated gene can then be inserted into an appropriate cloning vector. Vectors suitable for gene therapy include viruses, such as adenoviruses, adeno-associated virus (AAV), vaccinia, herpesviruses, baculoviruses and retroviruses, parvovirus, lentivirus, bacteriophages, cosmids, plasmids, fungal vectors and other recombination vehicles typically used in the art which have been described for expression in a variety of eukaryotic and prokaryotic hosts, and may be used for gene therapy as well as for simple protein expression.

In a preferred embodiment, the vector is a viral vector. Viral vectors, especially adenoviral vectors can be complexed with a cationic amphiphile, such as a cationic lipid, polyL-lysine (PLL), and diethylaminoethyldextran (DELAE-dextran), which provide increased efficiency of viral infection of target cells (See, e.g., PCT/US97/21496 filed Nov. 20, 1997, incorporated herein by reference). Preferred viral vectors for use in the present invention include vectors derived from vaccinia, herpesvirus, AAV and retroviruses. In particular, herpesviruses, especially herpes simplex virus (HSV), such as those disclosed in U.S. Pat. No. 5,672,344, the disclosure of which is incorporated herein by reference, are particularly useful for delivery of a transgene to a neuronal cell. AAV vectors, such as those disclosed in U.S. Pat. Nos. 5,139,941, 5,252,479 and 5,753,500 and PCT publication WO 97/09441, the disclosures of which are incorporated herein, are also useful since these vectors integrate into host chromosomes, with a minimal need for repeat administration of vector. For a review of viral vectors in gene therapy, see Mah et al., Clin. Pharmacokinet. 2002; 41(12):901-11; Scott et al., Neuromuscul. Disord. 2002; 12 Suppl 1:S23-9. In addition, see U.S. Pat. No. 5,670,488.

The coding sequences of the gene to be delivered are operably linked to expression control sequences, e.g., a promoter that directs expression of the gene. As used herein, the phrase "operatively linked" refers to the functional relationship of a polynucleotide/gene with regulatory and effector sequences of nucleotides, such as promoters, enhancers, transcriptional and translational stop sites, and other signal sequences. For example, operative linkage of a nucleic acid to a promoter refers to the physical and functional relationship between the polynucleotide and the promoter such that transcription of DNA is initiated from the promoter by an RNA polymerase that specifically recognizes and binds to the promoter, and wherein the promoter directs the transcription of RNA from the polynucleotide.

In one embodiment, a vector is used in which the coding sequences and any other desired sequences are flanked by regions that promote homologous recombination at a desired site in the genome, thus providing for expression of the construct from a nucleic acid molecule that has integrated into the genome (Koller and Smithies, Proc. Natl. Acad. Sci. USA. 1989, 86:8932 8935; Zijlstra et al., Nature 1989, 342:435 438).

In a specific embodiment, the vector is directly administered in vivo, where it enters the cells of the organism and mediates expression of the construct. This can be accomplished by any of numerous methods known in the art and discussed above, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell surface receptors or transfecting agents, encapsulation in biopolymers (e.g., poly-β-1-64-N-acetylglucosamine polysaccharide; see U.S. Pat. No. 5,635,493), encapsulation in liposomes, microparticles, or microcapsules; by administering it in linkage to a peptide or other ligand known to enter the nucleus; or by administering it in linkage to a ligand subject to receptor mediated endocytosis (see, e.g., Wu and Wu, J. Biol. Chem. 1987, 62:4429 4432), etc. In another embodiment, a nucleic acid ligand complex can be formed in which the ligand comprises a fusogenic viral peptide to disrupt endosomes, allowing the nucleic acid to avoid lysosomal degradation, or cationic 12 mer peptides, e.g., derived from antennapedia, that can be used to transfer therapeutic DNA into cells (Mi et al., Mol. Therapy. 2000, 2:339 47). In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188). Recently, a technique referred to as magnetofection has been used to deliver vectors to mammals. This technique associates the vectors with superparamagnetic nanoparticles for delivery under the influence of magnetic fields. This application reduces the delivery time and enhances vector efficacy (Scherer et al., Gene Therapy 2002; 9:102-9).

In a specific embodiment, the nucleic acid can be administered using a lipid carrier. Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature. 1989; 337:387). Intravenous injection of cationic lipid-plasmid complexes into mice has been shown to result in expression of the DNA in lung (Brigham et al., Am. J. Med. Sci. 1989; 298:278). See also, Osaka et al., J. Pharm. Sci. 1996; 85(6):612-618; San et al., Human Gene Therapy 1993; 4:781-788; Senior et al., Biochemica et Biophysica Acta. 1991; 1070:173-179); Kabanov and Kabanov, Bioconjugate Chem. 1995; 6:7-20; Liu et al., Pharmaceut. Res. 1996; 13; Remy et al., Bioconjugate Chem. 1994; 5:647-654; Behr, J-P., Bioconjugate Chem. 1994; 5:382-389; Wyman et al., Biochem. 1997; 36:3008-3017; U.S. Pat. No. 5,939,401 to Marshall et al; U.S. Pat. No. 6,331,524 to Scheule et al.

Representative cationic lipids include those disclosed, for example, in U.S. Pat. No. 5,283,185; and e.g., U.S. Pat. No. 5,767,099, the disclosures of which are incorporated herein by reference. In a preferred embodiment, the cationic lipid is N4-spermine cholesteryl carbamate (GL-67) disclosed in U.S. Pat. No. 5,767,099. Additional preferred lipids include N4-spermidine cholestryl carbamate (GL-53) and 1-(N4-spermine)-2,3-dilaurylglycerol carbamate (GL-89)

Preferably, for in vivo administration of viral vectors, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors. In that regard, it is advantageous to employ a viral vector that is engineered to express a minimal number of antigens.

Dosages

The amount of the small molecule analogue effective to stabilize the administered ASM protein and/or endogenous ASM mutant protein can be determined by those skilled in the art. Pharmacokinetics and pharmacodynamics such as half-life ($t_{1/2}$), peak plasma concentration ($C_{max}$), time to peak plasma concentration ($t_{max}$), exposure as measured by area under the curve (AUC), and tissue distribution for both the replacement ASM protein and the small molecule analogue as well as data for the small molecule analogue-replacement ASM protein binding (affinity constants, association and dissociation constants, and valency), can be obtained using ordinary methods known in the art to determine compatible amounts required to stabilize the replacement ASM protein, without inhibiting its activity, and thus confer a therapeutic effect.

Toxicity and therapeutic efficacy of the composition can be determined by standard pharmaceutical procedures, for example in cell culture assays or using experimental animals to determine the LD50 and the $ED_{50}$. The parameters LD50 and $ED_{50}$ are well known in the art, and refer to the doses of a compound that is lethal to 50% of a population and therapeutically effective in 50% of a population, respectively. The dose ratio between toxic and therapeutic effects is referred to as the therapeutic index and may be expressed as the ratio: $LD_{50}/ED_{50}$.

A therapeutically effective dose may be initially estimated from cell culture assays and formulated in animal models to achieve a circulating concentration range that includes the $IC_{50}$. The $IC_{50}$ concentration of a compound is the concentration that achieves a half-maximal inhibition of symptoms (e.g., as determined from the cell culture assays). Appropriate dosages for use in a particular individual, for example in human patients, may then be more accurately determined using such information.

Measures of compounds in plasma may be routinely measured in an individual such as a patient by techniques such as high performance liquid chromatography (HPLC) or gas chromatography.

The particular dosage used in any treatment may vary within this range, depending upon factors such as the particular dosage form employed, the route of administration utilized, the conditions of the individual (e.g., patient), and so forth.

According to current methods, the concentration of replacement ASM protein is between 0.05-5.0 mg/kg of body weight, typically administered weekly or biweekly. The protein can be administered at a dosage ranging from 0.1 μg/kg to about 10 mg/kg, preferably from about 0.1 mg/kg to about 2 mg/kg. For example, for the treatment of Fabry disease, the dose of clinically-approved recombinant α-Gal A administrated is typically between 0.1-0.3 mg/kg and is administered weekly or biweekly. Regularly repeated doses of the protein are necessary over the life of the patient. Subcutaneous injections maintain longer term systemic exposure to the drug. The subcutaneous dosage is preferably 0.1-5.0 mg of the α-Gal A per kg body weight biweekly or weekly. The ASM is preferably administered intravenously, e.g., in an intravenous bolus injection, in a slow push intravenous injection, or by continuous intravenous injection. Continuous IV infusion (e.g., over 2-6 hours) allows the maintenance of specific levels in the blood.

The optimal concentrations of the small molecule analogue will be determined according to the amount required to stabilize the recombinant ASM protein in vivo, in tissue or circulation, without preventing its activity, bioavailability of the small molecule analogue in tissue or in circulation, and metabolism of the small molecule analogue in tissue or in circulation. For example, the concentration of the small molecule analogue D-MAPP was determined by calculating the $IC_{50}$ value of the D-MAPP for the ASM, or less than 50 μM. Taking into consideration bioavailability and metabolism of the compound, concentrations around the $IC_{50}$ value or slightly over the $IC_{50}$ value can then be evaluated based on effects on ASM activity, e.g., the amount of small molecule analogue needed to increase the amount of ASM activity or prolong ASM activity of replacement ASM.

EXAMPLES

The present invention is further described by means of the examples, presented below. The use of such an example is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Example 1

Restoration of ASM Activity with D-MAPP

A small molecule, ceramide analogue known as D-MAPP (see FIG. 1 for structure) was evaluated as a potential ASSC for NPD.

Materials and Methods

D-MAPP was obtained from Matreya (Pleasant Gap, Pa., Cat. No. 1859) and reconstituted in ethanol at a concentration of 2 mM.

Recombinant ASM. In order to determine a non-inhibitory concentration range of D-MAPP that could be used to chaperone ASM, the $K_i$ was determined for purified, wild-type ASM. Recombinant, human ASM (rASM) was purified from the media of overexpressing Chinese Hamster ovary cells by published methods (He et al., Biochim et Biophys Acta. 1999; 1432:251-264). Briefly, this involved chromatography through DEAE Sephacel, Concanvalin A, and Superose 12. D-MAPP was obtained from Matreya Inc (Pleasant Gap, Pa. Cat. #1859).

Inhibition assays. For in vitro studies with the pure enzyme, an aliquot of the stock solution was dried under nitrogen, and then resuspended in sodium acetate buffer containing the fluorescent ASM substrate, BODIPY Sphingomyelin (Molecular Probes, Eugene Oreg.). The solution was sonicated, and an aliquot of pure, rASM was added. The final concentration of substrate in the assay was 100 micromolar ($\mu$M), and the concentration of D-MAPP varied from 10-500 $\mu$M. Assays were carried out as previously described (He et al., Biochem. 2003; 314: 116-120).

Type A NPD skin fibroblasts with two copies of the R496L mutation and normal skin fibroblasts were obtained (with informed consent), and cultured in a standard tissue culture medium (DMEM, GIBCO) containing 10% heat inactivated fetal calf serum. D-MAPP at various concentrations (from 5-50 $\mu$M) was added to the culture media and the cells were allowed to incubate for varying periods of time. At the end of the incubation, the cells were trypsinized, harvested with a rubber policeman, washed with saline, and resuspended in 10 mM Tris buffer, pH 7.0. A cell extract was prepared by sonication, the debris sonicated, and the supernatant was used for the determination of ASM activity using BODIPY Sphingomyelin as previously described (He et al., Biochem. 2003; 314: 116-120).

Results

Figure 4:
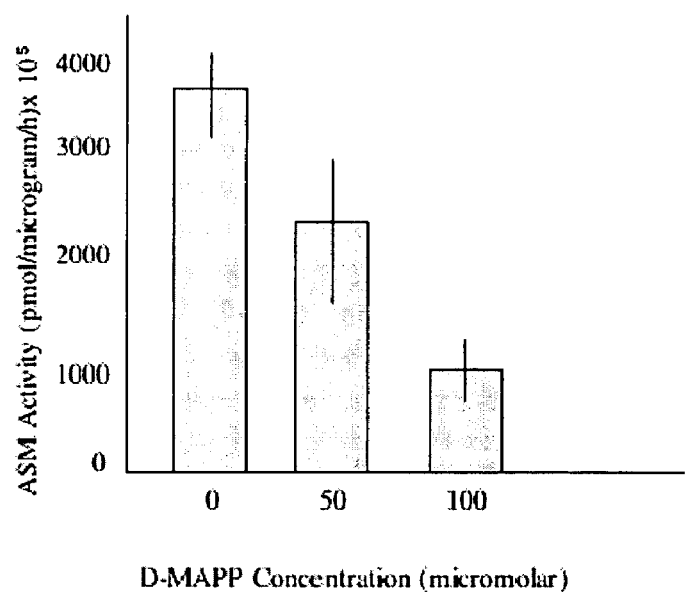
FIG. 4 demonstrates the KL of the inhibition of D-MAPP on wild-type ASM activity.
Figure 5:
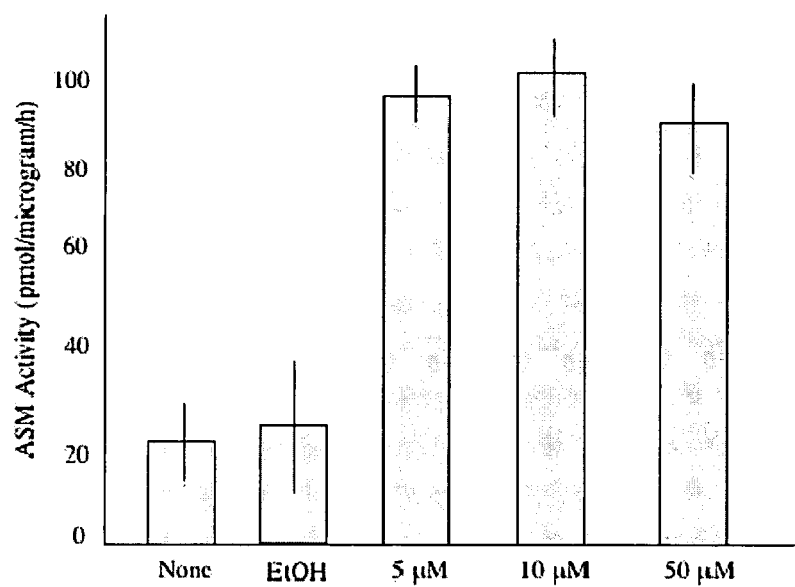
FIG. 5 shows the effect of D-MAPP on ASM activity in cells from an individual with Type A NPD.

FIG. 4 shows that D-MAPP inhibited the activity of pure ASM at a K of about 50 $\mu$M. FIG. 5 shows that when cultured skin fibroblasts from a patient with Type A NPD containing two copies of the R496L mutation were incubated in the presence of D-MAPP (5-50 $\mu$M) for three days, the residual ASM activity was enhanced up to 3-fold, or to about 3% of normal (from a starting activity of less than 1% of normal). Maximal enhancement was found at about 10 $\mu$M, and at this concentration there was no deleterious effects on cell growth or viability. Thus, D-MAPP, a small molecule inhibitor of wild-type ASM activity may be useful for as an ASSC for the treatment of NPD.

Example 2

Restoration of ASM Activity with a Novel Sphingomyelin Analogue

Materials and Methods

It is expected that the sphingomyelin analogues described herein will enhance normalASM activity, and rescue mutant ASM activity when administered to NPD fibroblasts, since these compounds are competitive ASM inhibitors (i.e., they reduce substrate binding-data not shown). Such sphingomyelin analogues are depicted in FIG. 2B-D. A preferred compound is the analogue depicted in FIG. 2D.

Recombinant ASM. The $K_i$ of the sphingomyelin analogue in FIG. 2D was determined for wild-type recombinant ASM as described above for D-MAPP.

Fibroblast assays. The $K_i$ of ASM inhibition in normal skin fibroblasts was also determined as described above for D-MAPP in NPD fibroblasts.

In addition, Type A NPD skin fibroblasts with two copies of the R496L mutation and normal skin fibroblasts will be treated with about 0.5-50 $\mu$M of the sphingomyelin analogues depicted in FIG. 2B-D for 5 days under the conditions described for D-MAPP above.

Results

The sphingomyelin analogue inhibited the activity of pure, recombinant ASM at a $K_i$ of about 70 $\mu$M, whereas it inhibited ASM in of normal skin fibroblasts by about 90% at 20 $\mu$M.

It is expected that these analogues will enhance wild-type activity similar to as shown for D-MAPP above. It is also expected that these analogues will rescue mutant ASM activity in mutant fibroblasts.

Example 3

Co-administration of a Small Molecule Analogue to Niemann-Pick Mice Treated Using Enzyme Replacement or Gene Therapy Materials and Methods and Results ASM deficient mice (NPD KO mice) have been generated previously (Dhami et al., Lab Invest. 2001; 81(7): 987-99). These mice are characterized by significantly higher number of cells in their pulmonary airspaces than normal mice by 10 weeks of age, consisting primarily of enlarged and often multinucleated macrophages. These mice can be used for experiments designed to demonstrate that a small molecule ceramide, sphingomyelin or nucleotide analogue, alone or in combination with gene therapy or enzyme replacement therapy could be useful for the treatment of NPD disease.

Enzyme replacement therapy for several lysosomal storage diseases has been developed by Genzyme Corporation, as well as Transkaryotic Therapies (TKT). It is expected that co-administration of D-MAPP, or other ceramide, sphingomyelin, or phosphonucleotide analogue (i.e., ASSC), such as those described herein, to ASM knock-out mice treated by infusion of the replacement enzyme will increase the stability, e.g., half-life, of the replacement enzyme in vivo, because the ASSCs stabilize the enzyme and prevent degradation. The small molecule analogue is orally administered to the KO mice after infusion of the wild-type ASM according to a similar protocol described previously for Fabry KO mice (Ioannu et al., Am J Hum Genet. 2001; 68:14-25). The ASM activity in various tissues including heart, kidney, spleen, liver, and lung as well as serum is determined over a period of time, and compared with those from the control mice that do not receive the ASSC, and mice that receive only the small molecule analogue but no enzyme. The extended time will indicate that co-administration of ASSC can improve the efficiency of enzyme replacement therapy.

Co-administration of the small molecule analogue to the ASM KO mice treated with gene therapy will increase the efficiency of the gene therapy, since it significantly improves the expression of the therapeutic gene product, specifically by preventing aggregation in the ER of the target cell. The KO mice following the gene therapy protocol receive D-MAPP or a sphingomyelin or nucleotide analogue as described herein, dissolved in drinking water and the small molecule analogue activity in various tissues including heart, kidney, spleen, liver, and lung as well as serum is determined over a period of time, and compared with those from the control mice that do not receive the small molecule analogue, and to mice that receive the small molecule analogue but not the gene therapy.

The higher enzyme activity and longer remaining time indicate that co-administration of the small molecule analogue can improve the efficiency of gene therapy.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, procedures, and the like are cited throughout this application, the disclosures of which are incorporated herein by reference in their entireties.

What is claimed:

1. A method of treating an individual having Niemann-Pick disease, or being genetically pre-disposed to developing Niemann-Pick disease, comprising administering to the individual a composition comprising a mutant acid sphingomyelinase (ASM) activity-enhancing amount of a compound wherein the compound is an inhibitor of wild-type ASM and is a ceramide analogue of Formula III:

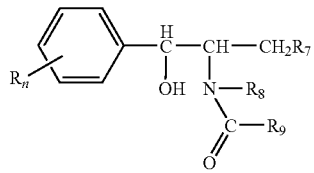

wherein $R_n$ is an independently optionally substituted $C_{1-10}$ alkyl, n=0-5, $R_7$ is H or OH, $R_8$ is H or $C_{1-10}$ alkyl, and $R_9$ is $C_{10-20}$ alkyl.

2. The method of claim 1, wherein the compound is D-MAPP, represented by the following structure:

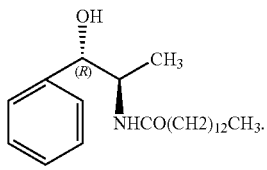

3. The method of claim 1, wherein the ASM mutant is L302 (SEQ ID NO: 3).

4. The method of claim 1, wherein the ASM mutant is R496L (SEQ ID NO: 2).

5. The method of claim 1, wherein the ASM mutant is delta R608 (SEQ ID NO: 4).

6. A method of enhancing the activity of a mutant acid sphingomyelinase (ASM) comprising administering a mutant ASM activity-enhancing amount of a compound to a diseased individual with Niemann-Pick disease or an individual who is genetically pre-disposed to Niemann-Pick disease, wherein the compound is a ceramide analog of Formula III:

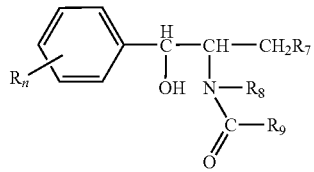

wherein $R_n$ is an independently optionally substituted $C_{1-10}$ alkyl, n=0-5, $R_7$ is H or OH, $R_8$ is H or $C_{1-10}$ alkyl, and $R_9$ is $C_{10-20}$ alkyl or a sphingomyelin analogue.

7. The method of claim 6, wherein the compound is D-MAPP, represented by the following structure:

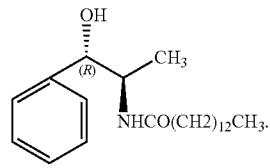

8. The method of claim 6, wherein the ASM mutant is L302 (SEQ ID NO: 3).

9. The method of claim 6, wherein the ASM mutant is R496L (SEQ ID NO: 2).

10. The method of claim 6, wherein the ASM mutant is delta R608 (SEQ ID NO: 4).

* * * * *

UNITED STATES PATENT AND TRADEMARK OFFICE
CERTIFICATE OF CORRECTION

| | | |
|---|---|---|
| PATENT NO. | : 7,750,050 B2 | Page 1 of 1 |
| APPLICATION NO. | : 10/998270 | |
| DATED | : July 6, 2010 | |
| INVENTOR(S) | : Edward H. Schuchman | |

It is certified that error appears in the above-identified patent and that said Letters Patent is hereby corrected as shown below:

Cover Page (74) Attorney, Agent or Firm, (column 2) – delete "Fish & RIchardson P.C." and insert -- Fish & Richardson P.C. --

Page 2, (column 1, line 13) – delete "may have" and insert -- has --

Claim 62, (column 37, line 17) – delete "alkyl or a sphingomyelin analogue." And insert -- alkyl. --

Signed and Sealed this
Eighth Day of February, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,750,050 B2 | |
| APPLICATION NO. | : 10/998270 | |
| DATED | : July 6, 2010 | |
| INVENTOR(S) | : Edward H. Schuchman et al. | |

It is certified that error appears in the above-identified patent and that said Letters Patent is hereby corrected as shown below:

Page 1, (column 1, line 11) – delete "This work was supported in part by NIH Grant No. HD28607. Pursuant to the terms of that grant, the federal government may have certain rights to this invention." and insert -- This invention was made with government support under grant No. HD28607 awarded by the National Institutes of Health. The government has certain rights in the invention. --

Signed and Sealed this
Fifteenth Day of March, 2011

David J. Kappos
*Director of the United States Patent and Trademark Office*